(12) United States Patent
Abildgaard (10) Patent No.: US 10,631,369 B2
(45) Date of Patent: Apr. 21, 2020

(54) INFRA-RED DEVICE FOR FOCUSED HEATING

(71) Applicant: IR Focus ApS, Skødstrup (DK)

(72) Inventor: Søren Stig Abildgaard, Skødstrup (DK)

(73) Assignee: IR FOCUS APS, Skødstrup (DK)

( * ) Notice: Subject to any disclaimer, the term of this patent is extended or adjusted under 35 U.S.C. 154(b) by 631 days.

(21) Appl. No.: 14/437,935

(22) PCT Filed: Oct. 29, 2013

(86) PCT No.: PCT/EP2013/072639
§ 371 (c)(1),
(2) Date: Apr. 23, 2015

(87) PCT Pub. No.: WO2014/067964
PCT Pub. Date: May 8, 2014

(65) Prior Publication Data
US 2015/0282252 A1    Oct. 1, 2015

(30) Foreign Application Priority Data
Oct. 29, 2012    (DK) ................. 2012 00666

(51) Int. Cl.
*H05B 3/00*     (2006.01)
*A61N 5/06*     (2006.01)
(Continued)

(52) U.S. Cl.
CPC ........... *H05B 3/008* (2013.01); *A61N 5/0625* (2013.01); *H05B 1/0275* (2013.01);
(Continued)

(58) Field of Classification Search
CPC .... A61F 2007/0088; A61N 2005/0642; A61N 2005/0651; A61N 2005/0659; A61N 2005/067; A61N 5/0625; F24H 2250/14; H05B 3/008; H05B 1/0275–0277; A47J 27/0802; A47J 36/32; A47J 27/004; A47J 43/046; A47J 43/0761; A47J 44/00
USPC ......... 392/355–356, 407–440; 700/207, 299, 700/300; 607/96, 98–102, 108–111; 219/411, 405, 121.65, 390, 494, 121.66,
(Continued)

(56) References Cited

U.S. PATENT DOCUMENTS 6,694,175 B1    2/2004  Califorrniaa
7,046,918 B1 *  5/2006  Burkett ................ F24H 3/0405
                                              126/110 R
(Continued)

FOREIGN PATENT DOCUMENTS

DE    4312400 A1    9/1993
EP    0872227 A2    10/1998
(Continued)

OTHER PUBLICATIONS

English translation of JP 2012026716A.*
(Continued)

*Primary Examiner* — Ibrahime A Abraham
*Assistant Examiner* — Chris Q Liu
(74) *Attorney, Agent, or Firm* — Cantor Colburn LLP (57) ABSTRACT

A heating system comprises at least one IR heating device 3 and at least one optical element arranged to focus or direct IR radiation emitted by the IR heating device 3 onto an object to be heated 1.

20 Claims, 2 Drawing Sheets

(51) Int. Cl.
*H05B 1/02* (2006.01)
*A61F 7/00* (2006.01)
*A61N 5/067* (2006.01)

(52) U.S. Cl.
CPC . *A61F 2007/0088* (2013.01); *A61N 2005/067* (2013.01); *A61N 2005/0642* (2013.01); *A61N 2005/0651* (2013.01); *A61N 2005/0659* (2013.01); *F24H 2250/14* (2013.01)

(58) Field of Classification Search
USPC ............ 219/121.67, 121.72, 121.73, 121.74, 219/121.8, 202, 203, 210, 213, 385, 386, 219/388, 395, 404, 408, 439, 444.1, 219/446.1, 448.11, 448.17, 451.1, 478, 219/480, 497, 501, 502, 520, 521, 528, 219/530, 533, 538, 539, 540, 548, 550, 219/552, 618, 759, 85.12
See application file for complete search history.

(56) References Cited

U.S. PATENT DOCUMENTS

| | | |
|---|---|---|
| 2003/0021596 A1 | 1/2003 | Salmon |
| 2004/0188396 A1* | 9/2004 | Talwar ................. B23K 26/032 219/121.65 |
| 2006/0065754 A1* | 3/2006 | Joergensen ......... F24D 19/1015 236/49.3 |
| 2007/0096352 A1 | 5/2007 | Cochran |
| 2010/0017953 A1 | 1/2010 | O'Keeffe |
| 2010/0080542 A1 | 4/2010 | Tartock |
| 2010/0150534 A1* | 6/2010 | Kasai .................. H01L 21/2686 392/416 |
| 2012/0206050 A1* | 8/2012 | Spero ...................... B60Q 1/04 315/152 |
| 2012/0239119 A1* | 9/2012 | Vyasarao ............. A61N 5/0625 607/88 |
| 2013/0259456 A1 | 10/2013 | Viswanathan |

FOREIGN PATENT DOCUMENTS

| | | |
|---|---|---|
| EP | 0919802 A2 | 6/1999 |
| GB | 2494635 A | 3/2013 |
| JP | 2003114029 A | 4/2003 |
| JP | 2012026716 A * | 2/2012 |
| WO | 2008038198 A2 | 4/2008 |

OTHER PUBLICATIONS

International Search Report for corresponding application PCT/EP2013/072639 filed Oct. 29, 2013; dated Apr. 16, 2014.
Written Opinion for corresponding application PCT/EP2013/072639 filed Oct. 29, 2013; dated Apr. 16, 2014.
British Examination Report for corresponding application GB1508173.0; Report dated Jun. 23, 2015.

* cited by examiner

INFRA-RED DEVICE FOR FOCUSED HEATING

The present invention relates to the field of heating, particularly heating for use in buildings.

Heating of homes today is, like any other energy uses, based on a very large and unsustainable consumption of fossil fuels. With the threat of climate change and ultimately depleted fossil reserves, it is necessary to find alternative solutions if we are to continue to keep the heat in our homes. There is great awareness of alternative energy sources as well as energy-efficient technologies that can reduce energy consumption in buildings. There are also major projects in progress on the development of zero-energy houses, programs for insulation, active and passive solar heating, etc.

However, there is also a large housing stock which is not realistic to insulate significantly and which will therefore remain with a great need for heating. Among other things, there is a very large number of older but attractive buildings which it will be difficult or impossible to insulate effectively without compromising the building's architecture and function. A concrete example of such buildings is older churches that require extremely high heating effects (supplies), if they are to be warmed up, and which often contain objects that will be damaged/dried by the heating. In many churches, there is thus a challenge around heating at fairs. In particular, there is at many churches an unsolved problem with regards to heating the organist when he/she must practice, and where the organist is alone in the church.

Church is just one example of the challenges that exist in heating many, especially older, buildings. Common to them is that the challenges only get bigger as the fossil fuels are phased out and energy supply must be based on alternative energy sources. It is primarily, but not exclusively, problems associated with buildings, such as those, that the proposed technology for heating seeks to address.

Here, firstly, is a description of the known forms of heating.

With the single most common form of heating, space heating, the temperature is maintained at a comfortable level, typically around 20° C. An advantage of this type of heating is that it can be supplied from so-called low-grade energy, which will include, among other things, the waste heat from thermal processes (eg. CHP) as a source of heating. A disadvantage of space heating is that a constantly heated room generates a corresponding constant heat loss from the building to the surroundings. Developments such as setback and zoning of the building only have a limited effect on this.

Another, but substantially less common, form of heating is radiant heat. Such systems are known mostly as outdoor heaters, also known as patio heaters, but are also used indoors, where among other things they can be useful in older buildings with cold bathrooms in the basement. The advantage of this type of heating system is that they provide immediate and almost instantaneous effect since the space as such is not warmed up. The downside is that the facilities for radiant heat usually require high energy consumption in the form of electricity if they are to be used indoors.

However, neither of the two known forms of heating, if necessary in combination, can fulfil modern requirements for comfort without simultaneous high power consumption. With the increasing pressure on fossil fuels, this calls for new solutions for heating to be significantly more energy efficient. There is, as mentioned, much research going into making homes more energy efficient and in many countries there are regulations for buildings that set requirements for the energy efficiency of buildings. Consequently, there are many well-developed methods for calculating the energy efficiency of a building, some of which are also used to determine the building's energy class (category), which is a measure of the building's energy efficiency. Common to the various methods is that they put building process energy consumption up against the building's size—typically measured in square metres. So, the less energy per square metre, the more energy efficient the building, and the better the energy class it achieves. Some of these methods recognise installations in the building for the production of electricity and heat as means for improving building efficiency, such as for example installation of CHP as an alternative to gas, that can provide a significant improvement of building energy obtained class. Calculations, measurements and analyses of a building's energy efficiency therefore provide a sound basis to evaluate different solutions for the energy of a building. Accomplished analyses can help to determine which initiatives will benefit the building's energy efficiency the most.

However, the inventor of the present application has made the observation that in parallel with the building's energy efficiency being calculated as a ratio between the size of the building and energy, the technological development is also seeing the building as an energy consumer, and aims to reduce the building's energy consumption. Within this context, technological developments within heating have had the goal to develop solutions that reduce building energy consumption related to heating.

A first aspect of the invention relates to a heating system comprising at least one IR (infra red) heating device and at least one optical element arranged to focus or direct IR radiation emitted by the IR heating device onto an object to be heated.

A second aspect relates to a method of heating an object using a heating system comprising at least one IR heating device and at least one optical element; the method comprising focusing or directing IR radiation emitted by the IR heating device onto the object to be heated with the optical element.

Thus, heat from an IR heating device is focused or directed onto an object to be heated using an optical element.

Since the heat from the IR heating device is focused or directed onto the object to be heated, heat may not be wasted by heating objects or areas other than the object to be heated. This can significantly reduce the amount of energy consumed in providing heating (e.g. to a building) since only certain desired objects may be heated, and not their surroundings.

Thus, it is preferred that only the object to be heated is heated by the IR heating device.

The system preferably further comprises a controller or control means arranged to control at least one of the at least one IR heating device and/or the optical element such that the IR radiation emitted by at least one of the IR heating device is focused or directed onto the object to be heated. For example, the controller could be arranged to turn at least one IR heating device on and/or off such that IR radiation is focused or directed (preferably solely) onto the object to be heated. Alternatively or additionally, the controller could be arranged to control the optical element to focus or direct IR radiation from the IR heating device onto the object to be heated. Alternatively or additionally, the controller could be arranged to control the at least one IR heating device (e.g. by moving, rotating or tilting it) such that its IR radiation is directed or focused onto the object to be heated.

The controller may be provided in the IR detector or it may be provided separately.

The controller should be in communication with the at least one IR heating device, e.g. such that it can send signals/information to the at least one IR heating device.

Preferably, the system (e.g. with a processor or processing circuitry) determines: (i) whether any IR radiation from the IR heating device is not focused or directed onto to the object to be heated; and/or (ii) whether all of the IR radiation from the IR heating device is focused or directed onto the object to be heated.

The system may then take steps to reduce, minimise or eliminate any wasted heating (i.e. heating from the IR heating device which is not focused or directed onto the object to be heated). For example, the IR heating device (or IR heating elements within the IR heating device) may be turned on or off, and/or the IR heating device (or IR heating elements within the IR heating device) could be moved and/or have their IR radiation focused/directed onto the object to be heated, and/or the optical element could be moved or adjusted to focus or direct the IR radiation onto the object to be heated.

The optical element could be any suitable optical element for directing or focussing IR radiation. For example, it could be or comprise a lens, e.g. a conventional lens, or it could be or comprise a mirror, for example.

The optical element may be movable (either with or separately from the IR heating device or an IR heating element in the IR heating device) so that IR radiation from the IR heating device may be directed or focused onto the object to be heated. For example, if a mirror is used as the optical element, this may be movable separately from a (e.g. fixed) IR heating device. However, if a lens is used as the optical element, this would in most cases not be movable relative to the IR heating device, although the IR heating device itself may be movable with the lens.

A single IR heating device may comprise a single or a plurality of IR heating elements (e.g. arranged in an array). In the case where the IR heating device comprises a plurality of IR heating elements, the whole IR heating device may be movable and/or the IR heating elements may be movable individually, such that the IR radiation may be directed and/or focused onto the target(s).

The object to be heated could be a person (or people), for example. However, in some situations it may be desirable to heat other objects (e.g. animals or other objects).

The system preferably comprises means for determining a location of the object to be heated. If the location of the object to be heated is determined, then heat from the at least one heating device can be focused or directed onto it accordingly. Thus, the system may also comprise means for directing or focusing heat from the at least one IR heating device onto the object to be heated based on the object's determined location.

The means for determining the location of the object to be heated may comprise at least one heat sensor, for example. However, in preferred embodiments, the means for determining the location of the object to be heated comprise at least one IR detector (also referred to as an IR receiver).

An IR detector is not necessarily used for determining the location of the object to be heated. Thus, the invention more generally may comprise at least one IR detector for detecting IR radiation emitted by the IR heating device. The system may comprise means for determining, based on IR radiation detected by the IR detector, the location of an object to be heated and/or whether IR radiation from the at least one IR heating device is striking an object to be heated.

The at least one IR detector may be arranged to detect the direction of IR radiation received at the detector and/or the intensity of the IR radiation.

The system may comprises means for distinguishing humans (or animals) from other objects, and preferably also determining their location. For example, the system may comprise one or more heat detectors. Additionally or alternatively, the system may comprise means for detecting skin or radiation emitted by or scattered off of skin. Skin usually has a very specific colour, especially in infrared wavelengths. This means that detectors that are capable of detecting such wavelengths may be used to distinguish humans from other objects and, preferably, also determine their location. In a preferred embodiment, a system comprises just one such means for distinguishing humans (e.g. in a particular room). Preferably, this means is only used to determine an initial location of the object to be heated (the human). The other IR detector(s) may then be used to determine its later location (e.g. if it moves).

In preferred embodiments, the at least one IR heating device (or IR heating elements thereof) is (are) arranged to flash periodically, preferably at a high frequency (e.g. 36 kHz). If at least one IR heating device (e.g. from a plurality of IR heating devices) flashes periodically (i.e. not all the time) then, based on this, the system can determine the location of an object to be heated and/or whether heat from the at least one IR heating device (that is flashing) is striking an object to be heated. The at least one heating device may then be controlled (e.g. turned on/off and/or moved) accordingly, e.g. to ensure that heat from the at least one heating device is provided only to the object to be heated.

A typical IR heating device (or element) may emit IR radiation with a wavelength (or a peak wavelength) of around 940 nm, for example. This wavelength will usually be the same for all IR heating devices in a system comprising a plurality of IR heating devices (and each IR heating device may itself have a plurality of IR heating elements). However, radiation with this wavelength (i.e. 940 nm) is also present in daylight as well as in many artificial light sources.

Each IR heating device (or element within a device) may also have a carrier frequency, i.e. a frequency at which the device (or element) may flash on and off.

Since radiation with a wavelength of 940 nm is present in daylight as well as from other IR heating devices/elements that may be being used (but not flashing), the carrier frequency may be used to distinguish IR radiation that is emitted from a particular (flashing) IR heating device (or element).

An IR heating device/element may flash at its carrier frequency periodically, e.g. for a certain period of time which may be referred to as a "burst".

The carrier frequency could be 36 kHz as for the RC-5 protocol, for example, or any other frequency from around 500 Hz upwards. Preferably, the carrier frequency is not more than 1 MHz as this would not provide any additional benefit.

Further, one cycle is then the period within which the IR heating device/element is first on and then off. For example, if the carrier frequency is 36 kHz, then the cycle length is $\frac{1}{36,000}$ s.

Usually, the IR heating device/element will be on at a constant (i.e. non-flashing) flux, or simply off. Preferably, only when the IR heating device (or an element thereof) is sending a message or signal, or when the success of said device (or an element thereof) to hit a target object is to be determined, will one or more IR elements of the device be flashing at the carrier frequency.

Preferably, the IR heating device (or an element thereof) may send signals with the IR radiation it emits. For example, a signal may comprise one or more bursts of IR radiation emitted at the carrier frequency and, preferably, of a length that is long enough to make that frequency evident at the receiver. For example, a burst may consist of 20 to 40, or around 32 cycles.

In a preferred embodiment, the IR heating device is arranged to send signals using a protocol developed for IR devices, such as the RC-5 protocol developed by Phillips. However, the signal protocol for the IR system could be this protocol or any other. In the case of the RC-5 protocol, the burst length is recommended to be 32 cycles.

The IR detector may be tuned to the carrier frequency (i.e. to detect signals sent at that frequency) with an internal filter, for example, such that it only detects incoming IR radiation at this frequency.

In some (e.g. special) cases, when sending a signal, the IR heating device/element may send one or more long bursts (e.g. longer than 32 cycles). This or these long bursts may then be used for other IR detectors to locate the target object and/or analyse the success of whether the IR radiation from the IR heating device/element hits the target object. When the burst is longer in duration, it is possible for a detector to make such an analysis with improved accuracy and precision.

Thus, in a preferred embodiment, an IR heating device/element can heat a target object while at the same time sending a signal. Furthermore, it can send a long burst when it is at the same time heating the object.

Similarly, an IR detector may receive the signal while it (or a processor in the system, e.g. in the IR detector or elsewhere) at the same time determines the direction of back-scattered light from the target object and calculates angles and/or the success/failure of the IR heating device to heat the target object, based on the received signal.

In this way, a continuous sequence of detecting the position of the target object from the back-scattered light, and sending signals between the IR heating devices/detectors may be provided.

In a preferred embodiment, a single IR device comprises one or more IR heating elements (e.g. LEDs) and one or more IR detectors. Each device preferably also comprises means to process (e.g. processing circuitry for processing) incoming data/signals (e.g. including those received from other IR devices in the system). Each device may comprise means to compute other IR heating device's success at hitting a target object from the back-scattered light received. This may normally only be when such back-scattered light is sent at the carrier frequency and so can be distinguished from other IR radiation received from other sources.

Preferably, only one IR heating device/element in a given system/at a given location (e.g. a room) will send a signal (e.g. by flashing at the carrier frequency) at any one time time, otherwise the signals may interfere with each other (since they use the same carrier frequency).

However, all IR detectors in a given system/at a given location (e.g. a room) may detect and read (or process) signals from any IR heating device/element in that system/at the given location and preferably can calculate from that their view on heating efficiency.

A system comprising an IR emitter and an IR receiver is used in most remote controls, for example, but requires a straight passage between the emitter and the receiver. However, IR emitters (heating devices/elements) used in the present invention are preferably of a much more powerful type than those used in remote controls. This is because their purpose is to heat and not merely to transmit information. This means that, in the present invention, back-scattered light should have sufficient intensity for the IR receiver/detector to be able to detect it. Such high power IR radiation is normally not used in other positioning detecting systems (since this would be a waste of energy). IR receivers/detectors are available which can detect IR radiation at a flux of $1$ $mW/m^2$, for example, IR heating is ideally provided at a flux of 10 to 100 $W/m^2$ from a single heating element (with a power of 10,000 to 100,000 mW) at the target and so should easily result in more than 1 $mW/m^2$ of back-scattered light at the IR receiver/detector.

Preferably, the IR heating device has a power rating which is high enough for heating objects (e.g. a person) in a room, and a light emitting intensity from an emitting area which is high enough to be used together with optics. For example, the IR heating device preferably emits IR radiation at around 1,000,000 $W/m^3$, or possibly higher. For safety reasons, the power of emitted IR radiation is preferably in the range of between 0.2 and 2 W, and so the die-size (emitting area) of a corresponding IR LED, for example, would be of the order of 1 $mm^2$.

The at least one IR heating device (or an element thereof) may comprise an IR laser. However, in preferred embodiments, the at least one IR heating device (or an element thereof) comprises an IR LED.

IR LEDs which are used for heating usually emit highly concentrated non-visible IR light which can be hazardous to the human eye. This may then lead to restrictions on the size of each IR LED for safety reasons. Preferably, there is a limit of around 100 $W/m^2$ of IR flux from each heating element arriving at the eye of a target person. If there is more than 100 $W/m^2$ from one heating element, then there may be an increased risk of damage to the eye. As a reference, sunlight has a flux of around 1000 $W/m^2$. However, the sum of the IR flux from multiple IR heating elements may be much higher than 100 $W/m^2$ without the risk of damaging the eye. This is because the radiation from each element focuses at a different place in the eye. Therefore, it is preferred that a heating device comprises a plurality of smaller LEDs, with preferably less than 5 W of IR radiation emitted from each LED in order to limit the risk. More preferably, there is not more than 2 W of IR radiation emitted from each LED. With 1 W of IR radiation emitted from each LED, the area of focused IR radiation on the target person should then be 0.01 $m^2$ or more.

It is an advantageous feature of LEDs that the light-emitting area of the LED is very small, since this makes it possible to use lenses (or other optical devices/elements) to focus or direct the light. The light-emitting area from lasers is actually much smaller than that from LEDs (it is basically a point) and they are therefore very well-suited and used for focusing light on a point at a far distance. However, this is also a safety risk if the laser is to be used for heating a body. This is because a failure in the lenses, or even a glass or other object with optical properties through which the IR radiation randomly passes, could potentially focus the light back into a point and result in a high thermal heat load to that point. This could light a fire, for example. However, there exists no such risk when using LEDs because the light-emitting area of an LED gives a physical restriction to how focused the light can be.

In addition, LEDs will emit light/heat without being warm themselves and they can work equally well at 20° C. as at 80° C., for example. This is firstly important to lenses since, in contrast to traditional IR heating elements that are warm (typically from 300 to 1000° C.), lenses may be attached directly to the IR LED element.

Another important issue is that of safety. Since the LED is not warm it can be placed in many places, e.g. where traditional infrared heating elements could not be placed. One such use could be as a heater in a car where IR LEDs could be placed under the instrument panel and steering wheel, for example, and provide heat to the driver and passenger, while a seat heater provides heat from the back. This could provide a very efficient heating system that would be particularly useful in e.g. battery/electric cars where efficiency is most important. Such a heating system may also be particularly useful in aeroplanes, for example, where each passenger could control their own temperature by controlling or adding heat from a focussed IR source, which the cabin temperature could be stabilised at a lower temperature, e.g. around 15° C.

In some embodiments, the system may further comprises a heating device (e.g. a conventional and/or space heater) arranged to heat an area in which the object to be heated is located. Such a heating device may be arranged to heat the area to a lower temperature, e.g. in a range of 5 to 15° C., preferably around 10° C. The heating device may be arranged to heat the area only during periods of high energy supply and/or to a higher temperature, e.g. up to 20° C., during periods of high energy supply. During periods of low energy supply, only the at least one IR heating device may be used, for example. This can provide a more energy-efficient heating system.

Preferably, each IR heating device has associated with it an IR detector (e.g. they are provided in pairs). The IR detector could be attached to or provided directly adjacent to the IR heating device for example. Alternatively, the IR detector(s) may be provided separately from the IR heating device(s).

As explained above, each IR heating element/device (e.g. LED) may have an IR output of around 1 W. This because, e.g. in the case that IR LEDs are used, they emit highly concentrated non-visible IR light which can be hazardous to the human eye. This then leads to restrictions on the size of each IR element (e.g. LED). Ideally, there should be a limit of around 100 $W/m^2$ of IR intensity from each heating element to the eye of a target person. Above 100 $W/m^2$ from one heating element there will be an increased risk of damage to the eye. However, the sum of the IR intensity from multiple IR heating elements may be much higher than 100 $W/m^2$ without a risk of damaging the eye since they focus at different places in the eye. Therefore, it is preferable that many smaller heating elements (e.g. LEDS) are used, with preferably less than 5 W of IR radiation emitted from each element to limit the risk. More preferably, there is not more than 2 W of IR radiation emitted from each element. With 1 W per element, the area of focused light on the target person/object should then be 0.01 $m^2$ or more to keep the intensity below 100 $W/m^2$. The area of the focused light increases with the square of the distance from light source to the target. Therefore the system should also work without a significant risk at a close distance and small area, hence the 0.01 $m^2$.

Effective heating for each person is ideally in the range of 20-200 W. (In some cases possibly up to 500 W). With just 1 W provided from each IR heating element, for example, this would mean that ideally 20-200 elements are provided in the system in order to provide adequate heat to one person. Of course, more elements may be provided if more than one person is to be heated by the system.

The elements may be arranged on/in heating devices. Each device may have, for example, around 5-50 IR heating elements. Preferably, the heating devices are located in places such that the heat to a person is provided from different directions to give the person the best possible comfort.

Certain features described above are considered to be independently inventive, thus, view from a further aspect, there is provided a heating system comprising at least one IR heating device and at least one IR detector, wherein the IR detector is arranged to detect the direction of IR radiation received directly and/or indirectly from the IR heating device.

Similarly, viewed from a further aspect, there is provided a method of heating an object using a heating system comprising at least one IR heating device and at least one IR detector, the method comprising detecting the direction of IR radiation received directly and/or indirectly from the IR heating device at the IR detector.

Thus, a system and/or method is provided in which an IR detector detects the direction of IR radiation received directly and/or indirectly from an IR heating device at the IR detector. This can allow, for example, determining whether or not the IR heating device is heating a desired object to be heated. The IR heating device may then be controlled accordingly, e.g. so that it only heats the object to be heated.

The system preferably further comprises means for determining the location of an object to be heated and/or whether heat from the at least one IR heating device is striking an object to be heated, based on the direction of IR radiation received at the IR detector. By determining the location of the object to be heated and/or whether heat from the at least one IR heating device is striking the object to be heated, the IR heating device may then be controlled accordingly, e.g. so that it only heats the object to be heated and heat is not wasted by heating other areas.

Thus, the system preferably further comprises a controller for controlling the at least one IR heating device based on the direction of the IR radiation received at the IR detector. The controller is preferably arranged to control the at least one IR heating device such that only the object to be heated is heated by the at least one heating device.

Viewed from a further aspect, there is provided a heating system comprising at least one IR heating device and at least one IR detector for detecting IR radiation emitted by the at least one IR heating device, wherein at least one of the at least one IR heating device is arranged to flash periodically.

Viewed from a further aspect, there is provided a method of heating an object using a heating system comprising at least one IR heating device and at least one IR detector, the method comprising detecting IR radiation emitted by the at least one IR heating device with the at least one detector, wherein at least one of the at least one IR heating device flashes periodically.

Thus, a system and/or method is provided with at least one IR heating device and at least one IR detector, wherein at least one of the at least one IR heating device is arranged to flash periodically.

By providing such a flashing IR heating device, this can allow the detection of IR radiation from a particular IR heating device and then that IR heating device can be controlled accordingly.

Preferably, the at least one of the at least one IR heating device is arranged to flash periodically at high frequency. This makes it easier to detect against background sources of IR radiation, or other constant (non-flashing) IR heating devices.

Preferably, the system further comprises at least one detector tuned to the frequency of IR radiation emitted by the at least one flashing IR heating device.

The system preferably further comprises means for determining the location of an object to be heated based on a frequency of IR radiation detected by the at least one detector. As described above, once the location of an object to be heated has been determined, the at least one IR heating device may then be controlled accordingly, e.g. to ensure that only the object to be heated is heated by the at least one IR heating device.

Viewed from a further aspect, there is provided a heating system comprising at least one IR heating device, a further heating device and a controller, wherein the controller is arranged to control the at least one IR heating device and the further heating device such that during periods of low energy supply only the at least one IR heating device is used to emit heat or the further heating device is arranged to emit heat at a lower level; and/or during periods of high energy supply, the further heating device is used to emit heat or the further heating device is arranged to emit heat at a higher level.

Viewed from a further aspect, there is provided a method of heating using a system comprising at least one IR heating device and a further heating device, the method comprising: during periods of low energy supply only using at least one IR heating device to emit heat or using the further heating device to emit heat at a lower level; and/or during periods of high energy supply using the further heating device to emit heat or using the further heating device to emit heat at a higher level.

Periods of high and low energy supply may be defined by setting an energy supply threshold (or more than one threshold) above/below which the time is designated as a period of high/low energy supply.

When the further heating device is arranged to emit heat at a lower level, this could be to heat a space to around 5-15° C., for example.

When the further heating device is arranged to emit heat at a higher level, this could be to heat a space to around 17-22° C., for example.

The further heating device could be a conventional heater such as a space heater, for example. It could be any form of heating providing non-focused heating.

The IR heating device preferably emits (focused) IR radiation onto an object to be heated (e.g. as described above) but preferably does not heat the surroundings.

Viewed from a further aspect, there is provided a building comprising a heating system according to any of the aspects described above.

Viewed from a further aspect, there is provided a vehicle (e.g. a road vehicle or an aeroplane) comprising a heating system according to any of the aspects described above.

The aspects of the invention described above may comprise any of the features (including optional and/or preferred features) of the other aspects of the invention described above.

The present invention takes here a new view with regard to heating. Instead of trying to reduce building energy consumption for heating, an aspect of the invention relates to a heating system characterised in that it is only the person or people in the building, which are sought to be heated. Instead of heating the entire building, the heat is focused on the person or persons (hereinafter simply person) in the building, while the heating of the building as such is not considered to have any value. Instead of heating the whole building, for example to 20° C., simply the person in the building is kept warm by solely focused heating, while the building itself remains cold (close to thermal equilibrium with the surroundings). The result will be that the heat loss from the building as a whole will be significantly reduced or eliminated, and will be "replaced" by an increased heat loss from the heated person to space (room, building), which is now colder. All in all, there will be a significant energy saving. There will even be a marked improvement of the building's energy efficiency, although it is no longer building's energy consumption being focused on but only heating the person in the building.

Focused warming could also be combined with space heating, where space heating is provided in such a way that the room is kept heated to only 10° C., for example, and thereby achieve significant energy savings compared to pure space heating but at the same time reduce the cost of installation of focused heating by continuing to use an existing heating system(s) for space heating.

With future energy characterised by renewable energy sources such as wind power, the supply of energy, and thus the price, may fluctuate greatly depending on the weather. A version of the heating system here may be characterised by a combination of (e.g. conventional space and/or radiant) heating and focused heating, and controlled so that during periods of large supply of energy heating is provided by the (e.g. conventional space and/or radiant) heating, while heating during periods of low supply of energy takes place (is provided) by focused heating. In this way, the energy in periods of increased supply may not only keep the person warm, but may also provide the special effect that the building itself during heating will accumulate heat and only slowly cool down again when the (e.g. central) heating is stopped. This can allow maximum utilisation of energy in times of plentiful supply as it exposes the need for heating during periods of low supply. At the same time, this may secure the system to the most energy-efficient means of heating, and the focused heat is used during periods of low supply.

A system for heating may be focused precisely depending on whether it can focus the heat yield on the person. This requires a method to control the heating system.

There are various ways to locate a person, for example heat locators/sensors which could be used to control the heating system. However, for the present invention there is developed a preferred alternative solution that may give better efficiency to the heating system.

The proposed alternative solution is a heating system characterised in that heat yield that is happening elsewhere than directly on the person is considered as waste, and the heating system is equipped with features to reduce this waste. By reducing this waste, the heating system in other words becomes better able to concentrate the heating of the person, and achieves a better energy efficiency. The better the heat is focused on the person, the less energy is wasted. The heating system therefore may be characterised in that it can detect the heat that does not hit the person and has methods (and/or means) to decrease the heat impinging on the side, up to the striking.

In addition, being able to locate the person and to direct heat at the person may also require a (e.g. at least one) heat source which is physically able to transfer heat to the person. Known technologies cannot achieve this effect to a sufficient extent. An aspect of the present invention thus concerns a single heating system characterised in that it uses infrared light (IR) or thermal radiation from IR LEDs. With IR LEDs, it is actually possible to focus the heat radiation on a person in the building, and thus only heat just the one who has the need.

An IR light-emitting diode emits heat radiation from a very small area, typically less than 1 mm$^2$, and in a narrow light spectra but over the visible wavelength. A typical IR LED emits light with a wavelength of 800-900 nm. This means that a common lens may be used to focus the radiation of heat but also that the thermal radiation is not visible to the eye. This also makes it possible to place the powerful IR LEDs a reasonable distance from the target/person, for example, 3 m, but still focus thermal radiation of the person, and thus reduce energy loss. This is in contrast to the known types of heating lamps and fittings for heat radiation, which function in that a filament or another material or gas is heated to a high temperature, often above 1000° C. When the temperature emitted thermal radiation, but the subject is also visibly glowing and must have a significant size in order to achieve a significant warming effect. In a home, the visible glow may be undesirable, but especially the necessary size of the glowing topic makes the technique unsuitable for focused heat radiation.

Another important feature of the IR LEDs relative to conventional radiant heat is their rapid response, i.e. time to turn on and off. Today, IR LEDs for remote controls, light-emitting diodes send messages by flashing, for example at 1500 Hz. Although IR light from a remote control is weak compared to the backlight, the IR receiver, due to the frequency, can distinguish remote infrared light from the backlight, and then decode the message. An aspect of the present invention is characterised in that it uses this property to determine whether the heat radiation from a LED hits a person, or simply the background according to the following principle.

Each infrared light emitting diode may be controlled so that it periodically flashes at a high frequency (e.g. 36 kHz). The frequency picked up by a number of IR receiver delegates, not directly from the IR LED, but from the object as thermal radiation environment. In addition to being sensitive to frequency, the IR receivers may also be of a type which can determine the direction of the IR light. The IR receiver may thus determine whether the thermal radiation from the IR LED has hit a known background, or whether it has hit a person between the IR LED and the background. The IR receiver may then answer the IR LED with a positive or negative signal, and the IR LED may then turn on or off depending on the answer.

Although the invention has been described particularly with regard to its use within buildings, it could be used in many other locations. For example, the invention could be used in vehicles such as cars, aeroplanes or other modes of transport.

Preferred embodiments of the invention will now be described by way of example only and with reference to the accompanying drawings, in which.

Figure 1:
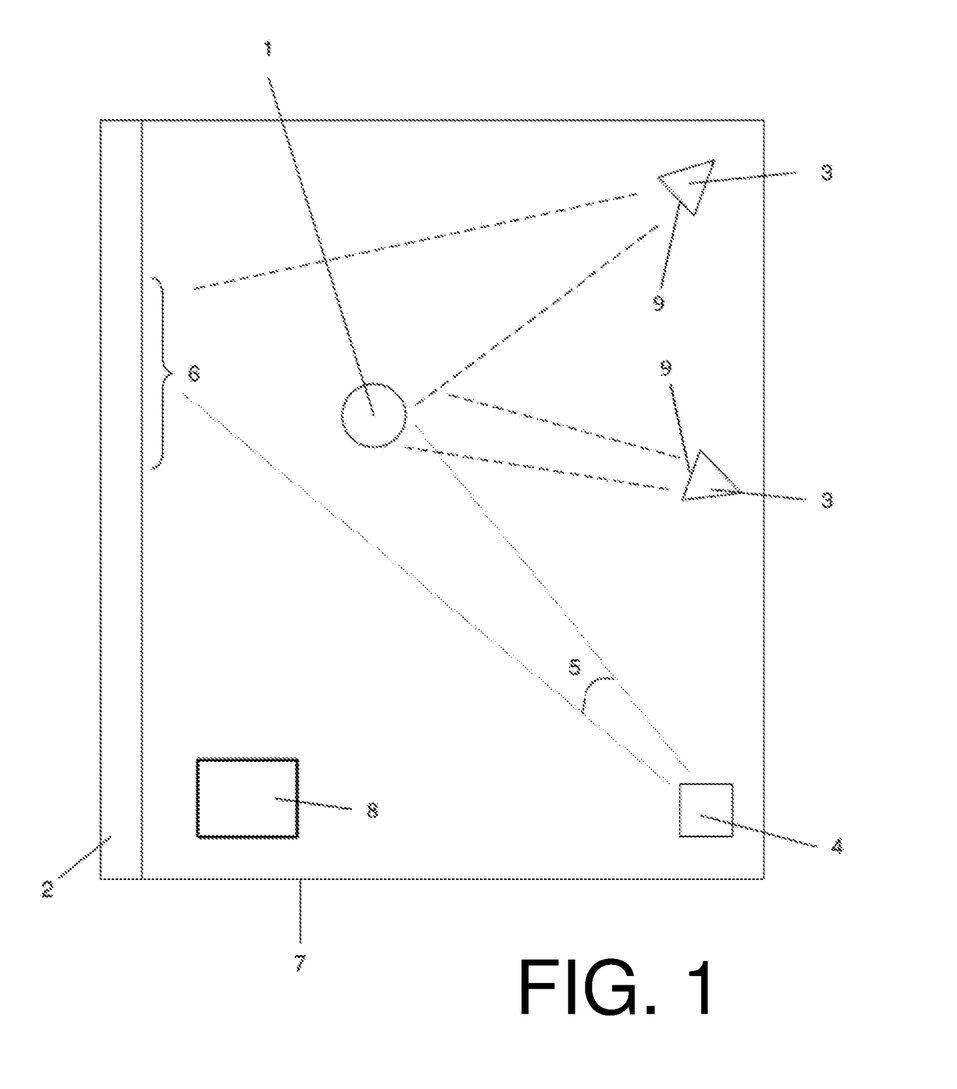
FIG. 1 is a schematic diagram of a heating system according to an embodiment of the invention.

FIG. 1 shows a heating system for focused heating based on IR light-emitting diodes as described above. In the space 7 is located a person 1 standing in front of a wall 2. The person 1 is heated by IR LEDs 3, which send heat radiation towards the person 1. Part of the radiation environment, however, next to 6, as detected by IR receiver 4 in that it can detect an angular difference 5 between IR light backscattered from the person 1 and the IR light that hits the wall 6.

The heating system with a space heater 8 and an optical element 9 as shown in FIG. 1 is provided in a room or space 7. FIG. 1 shows two IR LEDs 3 and a single IR receiver (or detector) 4. However, any number of these could be provided (and generally, many more would be to provide adequate heating). For simplicity, in this figure, only two IR LEDs 3 and a single IR receiver 4 are shown.

Each IR LED has a power of 1 W.

In alternatives embodiments, each IR LED 3 has associated with it, and located on it, an IR receiver 4 (i.e. they are not provided separately as in FIG. 1).

The IR LEDs 3 and IR receivers 4 are arranged about the space 7 in which the person 1 is located. For example, in a room, they may be located on the ceiling. In this case, the IR LEDs 3 are arranged at a 45° angle to the horizontal so that they can heat both the top and the sides of the person 1 in the room 7.

Each IR LED 3 has a lens fixed to it for focusing the IR radiation emitted by the IR LED. The IR LEDs 3 with their lenses can each be moved to direct or focus their IR radiation onto the person 1.

As shown in FIG. 1, all of the IR radiation emitted by one of the IR LEDs 3 strikes the person 1. However, some of the IR radiation from the other IR LED 3 passes the person 1 and is back-scattered off the wall 2 at region 6.

The IR receiver 4 detects the IR radiation which is backscattered from the person 1 as well as that from the region 6 of the wall 2. The IR receiver 4 can detect the direction of the back-scattered radiation and, based on this, the angular difference 5 between the IR radiation scattered off of the person 1 and the IR radiation scattered off of the region 6 of the wall 2 can be determined.

The IR LEDs 3 can then be controlled accordingly (by a controller) so that only the person 1 is heated by the LEDs 3 and not the wall 2 or other surroundings. For example, the or some IR LEDs 3 could be turned off and/or their direction could be changed (e.g. by moving one or more mirrors, lenses, and/or the IR LEDs themselves) to ensure that the emitted IR radiation only hits the target person and that sufficient (but not too much) heat is provided to the target person.

The controller is provided in the IR receiver 4 and is arranged to communicate (i.e. send signals to) the IR LEDs 3 so that they can be controlled.

In an embodiment, the IR LEDs 3 are positioned in arrays (e.g. a number of IR LEDs located along a bar) provided on a ceiling in a room. The IR LEDs are pointed at 45° to the horizontal to ensure that the person being heated is heated not only from above but also on their sides.

In an embodiment, the system also comprises a further heating device (e.g. a conventional and/or space heater) which is arranged to heat the space 7 in which the target object 1 is located. The further heating device is arranged to heat the space 7 to a lower temperature, e.g. around 10° C. The heating device may be arranged to heat the space 7 only during periods of high energy supply and/or to a higher temperature, e.g. up to 20° C., during periods of high energy supply. During periods of low energy supply, only the at least one IR heating device 3 is used, for example.

Figure 2:
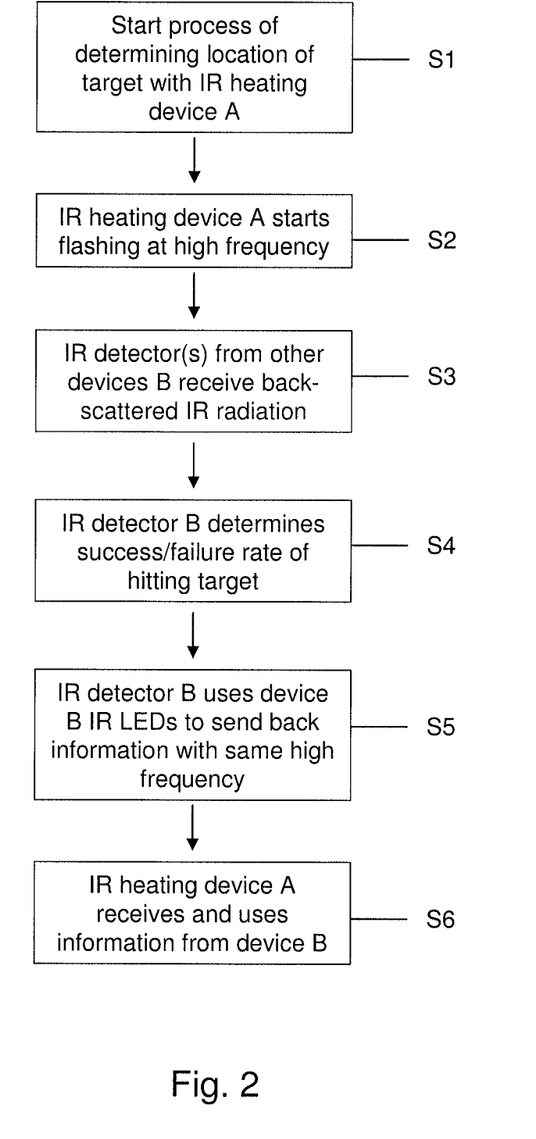
FIG. 2 is a flow diagram illustrating a method according to an embodiment of the invention.

FIG. 2 shows a flow diagram of a process according to an embodiment of the invention.

In this process, IR light is emitted from an IR heating device A (IR LED). The IR heating device A starts the process of determining the location of a target (step S1). During the process of determining the direction of the target person from that IR device, the IR device A is made to flash at a high frequency, e.g. 36 kHz (step S2). Some of the IR radiation from the device hits the background and misses the target person. Some of the target person is hit.

There could be many IR heating devices provided in a system but, preferably, only one at a time is in the process of localising (i.e. determining the location of) the target person (i.e. by flashing).

A IR detector B detects the backscattered IR radiation from the target person and from the background (step S3). The detector B is tuned to the flashing frequency (it contains a filter to filter out other frequencies), e.g. 36 kHz, so it is able to distinguish IR radiation received from the flashing heat source A from that from other IR heat sources and other (background) IR radiation.

The IR detector B can detect the intensity and direction of the backscattered light. Based on this, it can determine how effectively the IR heating device A is heating the person to be heated, e.g. if any heat is missing the target person (step S4). The location of the target person can also be determined. The IR LED(s) associated with the detector B then send this information back to the IR LED A using the same high frequency IR signal (step S5). The IR heating device A may then be controlled (e.g. turned off or moved) or an optical element may be controlled to focus or direct IR radiation from the IR heating device A (solely) onto the person to be heated (step S6).

The invention claimed is:

1. A heating system for use in providing heating of persons in a building, the system comprising:
   a processing circuitry
   at least one IR heating device;
   at least one optical element arranged to focus or direct IR radiation emitted by the IR heating device onto a person to be heated; and
   at least one IR detector configured to detect IR radiation received directly from the IR heating device or IR radiation received indirectly from the IR heating device,
   wherein the at least one IR detector is tuned to the carrier frequency; and
   wherein the processing circuitry is configured to:
      control the at least one IR heating device to flash on and off in bursts at a carrier frequency;
      identify IR radiation that is emitted from the flashing IR heating device and distinguish IR radiation from that of other IR heat sources and other background IR radiation; and
      detect the direction of the IR radiation received from the IR heating device or IR radiation received indirectly from the IR heating device according to the carrier frequency.

2. A heating system as claimed in claim 1, wherein the optical element comprises a lens or a mirror.

3. A heating system as claimed in claim 1, wherein the at least one IR detector is arranged for determining a location of the person to be heated.

4. A heating system as claimed in claim 1, wherein the at least one IR heating device comprises an IR LED or an IR laser.

5. A heating system as claimed in claim 1, further comprising a further heating device arranged to heat an area in which the person to be heated is located.

6. A heating system as claimed in claim 5, wherein the further heating device is a space heater.

7. A heating system as claimed in claim 5, wherein the further heating device is arranged to heat the area to a temperature in a range of 5 to 15° C.

8. A heating system as claimed in claim 5, wherein the further heating device is arranged to heat the area only during periods of high energy supply to the building.

9. A building comprising a heating system as claimed in claim 1.

10. A heating system as claimed in claim 1, wherein the carrier frequency is at a frequency of 500 Hz or greater.

11. A method of heating a person in a building, the method using a heating system comprising: at least one IR heating device arranged to flash periodically at a carrier frequency, at least one optical element, and at least one IR detector configured to detect IR radiation received directly from the IR heating device or IR radiation received indirectly from the IR heating device, wherein the at least one IR detector is arranged to detect a direction of the received IR radiation; the method comprising:
   focusing or directing IR radiation emitted by the IR heating device onto the person to be heated with the optical element, wherein the heating device is flashing on and off;
   detecting IR radiation received directly or indirectly from the IR heating device with the at least one IR detector;
   identifying IR radiation that is emitted from the flashing IR heating device and distinguishing IR radiation from that of other IR heat sources and other background IR radiation;
   detecting the direction of the received IR radiation with the at least one IR detector; and using the carrier frequency to identify IR radiation that is emitted from the periodically flashing IR heating device.

12. A method as claimed in claim 11, further comprising determining a location of the person to be heated.

13. A method as claimed in claim 11, wherein the at least one IR heating device is arranged to flash periodically, preferably at a high frequency.

14. A method as claimed in claim 11, wherein the at least one IR heating device comprises an IR LED or an IR laser.

15. A method as claimed in claim 11, further comprising heating an area in which the object to be heated is located with a further heating device.

16. A method as claimed in claim 15, wherein the further heating device comprises a space heater.

17. A method as claimed in claim 15, wherein the area is heated with the further heating device to a temperature in a range of 5 to 15° C.

18. A method as claimed in claim 15, wherein the heating device is arranged to heat the area only during periods of high energy supply to the building.

19. A method as claimed in claim 11, further comprising controlling the at least one IR heating device based on the direction of the IR radiation received at the IR detector.

20. A method as claimed in claim 11, wherein the at least one IR heating device is controlled such that only the person to be heated is heated by the at least one heating device.

* * * * *